United States Patent
Valentine et al.

(10) Patent No.: US 6,681,622 B1
(45) Date of Patent: Jan. 27, 2004

(54) DEVICE FOR AND METHOD OF DETERMINING CUT RESISTANCE OF A MATERIAL

(75) Inventors: Bethanne L. Valentine, Freeland, MI (US); Lawrence C. Stanos, Midland, MI (US); Bryan L. Ackerman, Freeland, MI (US)

(73) Assignee: S.C. Johnson Home Storage, Inc., Racine, WI (US)

(*) Notice: Subject to any disclaimer, the term of this patent is extended or adjusted under 35 U.S.C. 154(b) by 0 days.

(21) Appl. No.: 10/284,583

(22) Filed: Oct. 31, 2002

(51) Int. Cl.$^7$ .............................................. G01N 03/56
(52) U.S. Cl. ............................. 73/159; 73/104; 73/105; 73/78; 73/783; 73/7
(58) Field of Search ........................... 73/104, 105, 78, 73/783, 159, 7

(56) References Cited

U.S. PATENT DOCUMENTS

| | | | |
|---|---|---|---|
| 1,780,822 A | | 11/1930 | Honda |
| 1,983,597 A | | 12/1934 | Casselman |
| 2,055,125 A | | 9/1936 | Floyd |
| 2,436,435 A | * | 2/1948 | Kent .............................. 73/85 |
| 2,472,994 A | | 6/1949 | Vars |
| 2,481,467 A | * | 9/1949 | Bloom et al. ................... 73/78 |
| 3,026,726 A | * | 3/1962 | Reading ....................... 73/159 |
| 3,785,201 A | * | 1/1974 | Rubio et al. ................... 73/169 |
| 3,817,090 A | | 6/1974 | Michel |
| 3,827,281 A | | 8/1974 | Hamel |
| 4,691,576 A | * | 9/1987 | Schleuniger et al. ........... 73/821 |
| 4,791,807 A | * | 12/1988 | Oechsle .......................... 73/78 |
| 4,864,852 A | | 9/1989 | Boone |
| 4,934,185 A | | 6/1990 | Nishiyama et al. |
| 4,958,511 A | * | 9/1990 | Marcus ............................ 73/7 |
| 5,597,649 A | | 1/1997 | Sandor et al. |
| 5,698,769 A | * | 12/1997 | Hupf ............................... 73/7 |
| 6,274,232 B1 | | 8/2001 | Otten et al. |
| 6,383,614 B1 | | 5/2002 | Carson et al. |
| 6,383,615 B2 | | 5/2002 | Otten et al. |
| 6,391,806 B1 | | 5/2002 | Carson et al. |

FOREIGN PATENT DOCUMENTS

WO    WO 00/78536 A1    12/2000

OTHER PUBLICATIONS

AMS Test Method D 3822–01 entitled "Standard Test Method for Tensile Properties of Single Textile Fibers", West Conshohocken, PA 19428–2959, pp. 1–11.

AMST Test Method F 1790–97 entitled "Standard Test Method for Measuring Cut Resistance of Materials Used in Protective Clothing", West Conshohocken, PA 19428–2959, pp. 1–6.

Web page: CATRA—Razor Edge Durability & Sharpness Test "Razor Edge Durability and Sharpener Tester" (3 pages).

* cited by examiner

*Primary Examiner*—Hezron Williams
*Assistant Examiner*—Katina Wilson

(57) ABSTRACT

A device implements a method of determining a cut resistance of a sample. The device includes a blade wherein the blade and the sample are relatively movable and a first apparatus that transfers energy to at least one of the sample and the blade to cause relative movement thereof in a direction parallel to a surface of the sample such that the blade contacts and cuts the sample until the imparted energy is expended and relative movement is terminated. A second apparatus measures a parameter of the relative movement to obtain an indication of the cut resistance of the sample.

33 Claims, 12 Drawing Sheets

FIG. 5
FIG. 4A
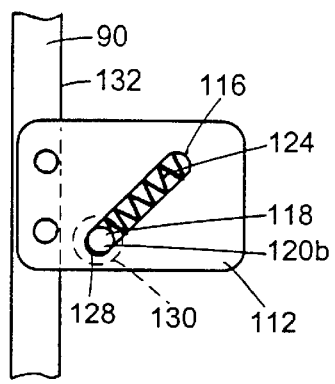
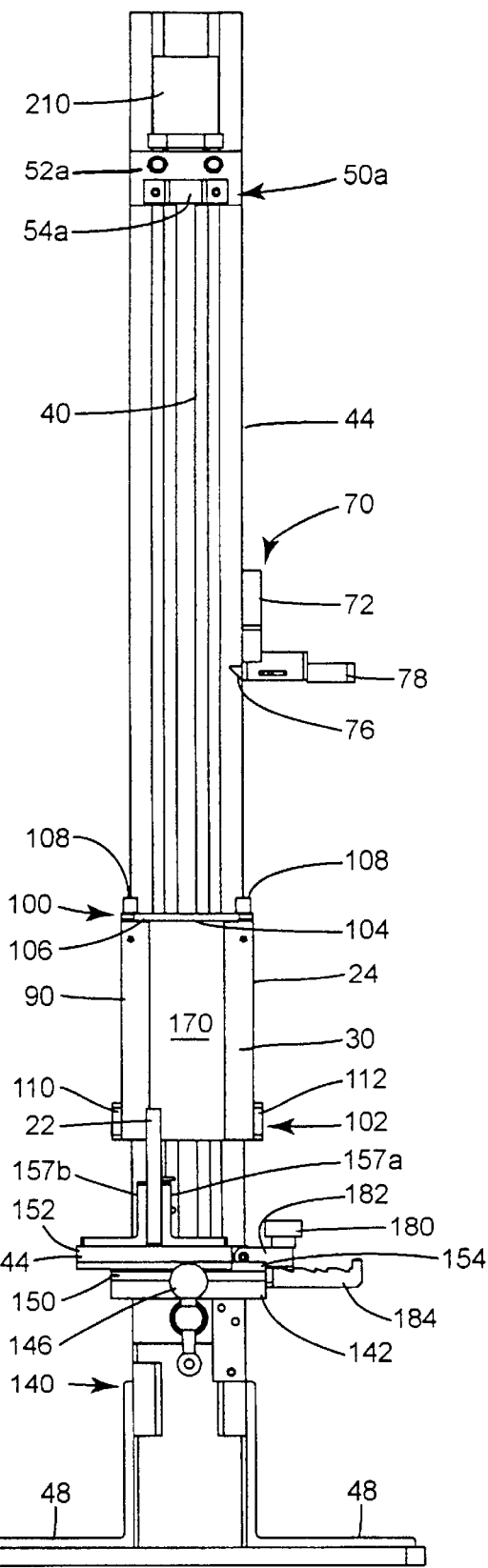

DEVICE FOR AND METHOD OF DETERMINING CUT RESISTANCE OF A MATERIAL

TECHNICAL FIELD

The present invention relates generally to methods and apparatus for determining the cut resistance of materials, and more particularly to a method and apparatus for determining the cut resistance of a film or sheet.

BACKGROUND ART

The use of disposable cutting boards or surfaces for preparation of food or other articles is well known. Depending on the use of the cutting boards or surfaces, a specific cut resistance may be necessary. In such cases, testing must be performed in order to produce a product with the necessary cut resistance. Several testing methods have been developed for measuring the cut resistance of materials.

ASTM Test Method F 1790-97 entitled "Standard Test Method for Measuring Cut Resistance of Materials Used in Protective Clothing" discloses a method and apparatus for measuring the cut resistance of various protective materials. The test instrumentation includes a cutting blade mounted on a motor-driven balanced arm. A known load is applied to the arm and brought into contact with a specimen mounted on a mandrel. The arm is moved relative to the specimen and the distance that the arm moves relative to the specimen until the point at which cut-through of the specimen occurs is measured. This process is repeated for several different loads and the resulting force-distance data is used to determine various tensile properties of the material. Because the cutting blade only stays in contact with a highly localized point of a specimen during the test, the method and apparatus are only suitable for measuring the cut resistance of homogeneous products.

ASTM Test Method D 3822-01 entitled "Standard Test Method for Tensile Properties of Single Textile Fibers" discloses a test method for measuring the tensile properties of man-made single textile fibers. A single-fiber specimen of sufficient length to permit mounting in a tensile machine is placed under increasing tensile forces until breakage of the fiber occurs. Various tensile properties are calculated from the test results.

Boone U.S. Pat. No. 4,864,852 discloses a method and apparatus for measuring the cut-resistance of flexible materials such as films, fabrics, felts, and papers. The apparatus includes a material wrapped around a mandrel that is rotating at a predetermined speed and a cutting edge that repeatedly falls on the material covering the mandrel. The cutting edge falls in the same spot and with the same force until it cuts through the material and makes electrical contact with the mandrel. The number of times that the cutting edge contacts the material until the edge contacts the mandrel is noted and used as a measure of the relative cut resistance of the material.

Nishiyama et al. U.S. Pat. No. 4,934,185 discloses a device for measuring the adhesive strength and shear strength of coated films. The device includes a cutting blade placed under a certain load and at a certain rake angle, wherein the load causes the blade to move in a vertical direction to penetrate the surface of the coated film and the load and rake angle cause the blade to slice the coating on the film. A cutting force of the blade is measured by a pressure detector and a vertical displacement of the blade is measured by a differential transducer, and the resulting data are used by a personal computer to calculate the adhesive strength and shear strength of the coated film.

Otten et al. U.S. Pat. No. 6,274,232 discloses an absorbent sheet material and an apparatus for testing the slice resistance thereof. The apparatus includes a knife blade disposed in a knife holder and a sample mounted on a platform and disposed below the knife holder. A known load is applied to the knife blade in the vertical direction and the platform is moved under the weight of the knife blade. A series of slices under increasing load are made until the knife cuts through the sample and slice resistance is calculated as the slice force per sample thickness.

SUMMARY OF THE INVENTION

According to one aspect of the present invention, a device for determining the cut resistance of a sample includes a blade wherein the blade and the sample are relatively movable and a first apparatus that transfers energy to at least one of the sample and the blade to cause relative movement thereof in a direction parallel to a surface of the sample such that the blade contacts and cuts the sample until the imparted energy is expended and relative movement is terminated. A second apparatus measures a parameter of the relative movement to obtain an indication of the cut resistance of the sample.

According to a further aspect of the present invention, a device for determining cut resistance of a material includes a sample holder having a known mass wherein the sample holder is adapted to receive a sample of the material and a blade. Guide apparatus is provided for effecting relative movement of the sample holder and the blade holder under the influence of gravity along a path from a particular initial position wherein the material sample is out of contact with the blade and a final position wherein the material sample is in stationary contact with the blade thereby forming a cut having a cut length in the sample. Measurement apparatus is also provided for indicating a length of the path, the path length and the cut length being used to obtain an indication of cut resistance.

According to yet another aspect of the present invention, a method of determining a cut resistance of a material comprises the steps of providing a sample of the material and a blade wherein the sample and the blade are relatively movable and imparting energy to at least one of the sample and the blade to cause relative movement thereof in a direction parallel to a surface of the sample such that the blade contacts and cuts the sample until the imparted energy is expended and relative movement is terminated. A parameter of the relative movement is measured to obtain an indication of the cut resistance of the sample.

According to a still further aspect of the present invention, a method of determining a cut resistance of a material includes the steps of providing a movable sample holder having a known mass wherein the sample holder is adapted to receive a sample of the material and providing a stationary blade holder and a blade mounted to the blade holder. The movable sample holder is positioned at a predetermined height above the blade. The movable sample holder is released to cause the sample holder to move under the influence of gravity until the sample contacts the blade and is cut thereby for a cut distance until movement of the sample holder is terminated. The cut distance and the predetermined height are used to obtain an indication of the cut resistance of the sample.

According to yet another aspect of the present invention, According to yet another aspect of the present invention, a method of determining cut resistance inhomogeneity of a material includes the steps of providing a sample of the material and a blade wherein the sample and the blade are relatively movable and imparting energy to at least one of the sample and the blade to cause relative movement thereof in a direction parallel to a surface of the sample such that the blade contacts and cuts the sample until the imparted energy is expended and relative movement is terminated. The position of at least one of the sample and the blade is measured to obtain an indication of the local inhomogeneity of cut resistance of the sample.

Other aspects and advantages of the present invention will become apparent upon consideration of the following detailed description.

BRIEF DESCRIPTION OF THE DRAWINGS

FIG. 4a is an enlarged fragmentary, front elevational view of a portion of the device of FIG. 3;

FIG. 5 is a side elevational view of the device of FIG. 3;

FIGS. 10–12 are fragmentary isometric views of the apparatus of FIG. 2 during a testing procedure wherein FIGS. 10 and 11 show the sample holder at the beginning of creation of a cut or slice and FIG. 12 shows the sample holder at the end of a cut or slice operation.

DESCRIPTION OF THE PREFERRED EMBODIMENTS

Figure 1:
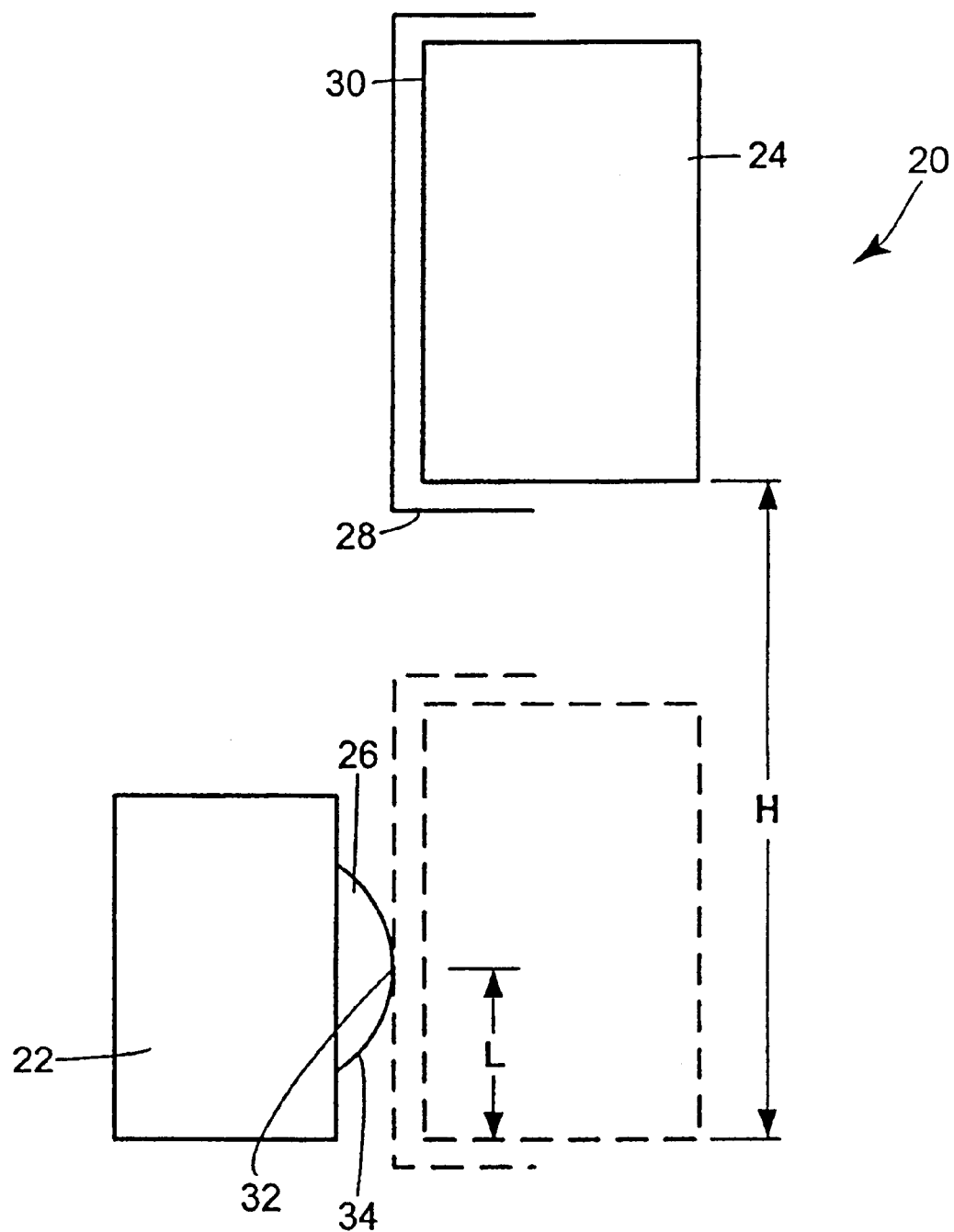
FIG. 1 is a block diagram illustrating a device for determining cut resistance according to the present invention.

Referring first to FIG. 1, a device 20 according to the present invention is diagrammatically shown and includes a stationary blade holder 22 and a movable sample holder 24. Although not shown in FIG. 1, guide apparatus is provided (described in greater detail hereinafter) that guides the sample holder 24 and constrains same to move in a substantially vertical linear path with respect to the stationary blade holder 22. Preferably, the sample holder 24 has a known mass and is guided for movement between a first or upper travel limit and a second or lower travel limit. As noted in greater detail below, the first or upper travel limit may be selectable. When the sample holder 24 is disposed at the first or upper travel limit the sample holder 24 is positioned at a known or selectable predetermined height above and out of contact with a cutting portion of a blade 26 mounted on the blade holder 22. Preferably, at initiation of a testing procedure, a sample 28 of a material is mounted on a side surface 30 of the sample holder 24 and the sample holder 24 is moved to the upper travel limit. The sample holder 24 is then released and moves downwardly along the substantially vertical linear path under the force of gravity. In accordance with the preferred embodiment, and as noted in greater detail hereinafter, the sample 28 has a thickness T and a horizontal distance between the side surface 30 and an outermost portion 32 of an edge 34 of the blade 26 is less than the thickness T. Therefore, downward movement of the sample holder 24 during a testing procedure results in contact of the sample 28 with the edge 34 and creation of a cut or slice in the sample 28. The first or upper travel limit is selected such that the change in potential energy of the sample holder 24 and the sample 28 throughout a test is a substantial fraction of the energy required to cut the full length of the sample 28, but less than 100% of this energy. Assuming that the first or upper travel limit is properly selected, the potential energy that is converted into kinetic energy of the sample holder 24 and the sample 28 is eventually used up by the drag imparted by the cut or slice resistance of the sample 28 and the sample holder 24 and the sample 28 stop moving relative to the blade 26. At this point the sample holder 24 is disposed at the second or lower travel limit with the sample 28 in stationary contact with the blade 26. The length L (expressed in centimeters) of the cut or slice in the sample 28 and the height H (expressed in meters) that the sample block traveled between the first and second travel limits are used in the following equation to calculate the energy per unit length E/L (in joules per centimeter) expended by the resisting force of the blade 26 with the sample 28:

$$E/L = mgH/L$$

where m is the combined mass of the sample holder 24 and the sample 28 in kilograms (which may be approximated by the mass of the sample holder 24 alone if the mass of the sample 28 is negligible) and g is the gravitational constant (equal to 9.8 meters per second squared) and where frictional losses between the sample holder 24 and the guide apparatus are small and are consistent between test cycles. The value E/L is used as an indication of the cut or slice resistance or the sample 28.

If desired, the local cut resistance inhomogeneity of a sample may be indicated by recording the position of the sample holder 24 versus the time elapsed during a test provided the time intervals between measurements are suitably small (e.g. 1 millisecond). The component of cutting force F, in the direction of movement (in Newtons) versus time may be calculated using the temporal position data collected during the cutting portion of the test and the equation:

$$F_c = F_{net} - F_g = ma - mg = m(dv/dt - g) = m(d^2x/dt^2 - g)$$

where m and g are defined as before, $F_{net}$ is the net force of the sample on the knife in the direction of sample holder 24 movement (in Newtons) or the net force of the knife on the sample in the direction opposed to sample holder 24 movement per Newton's Third Law of Motion, $F_g$ is the gravitational force on the sample holder 24 and sample 28 (in Newtons), a is the acceleration (deceleration if negative) of the sample holder 24 and sample 28 (in meters per second squared), dv/dt is the time derivative of the velocity of same (in meters per second squared), and $d^2x/dt^2$ is the second time derivative of position of same (in meters per second squared). For computational purposes, one of the finite difference forms of this equation would be employed. For example, the 3-point central difference form of the equation is one useful version:

$$F_c[i] = m((x[i+1] - 2x[i] + x[i-1])/\Delta t^2 - g)$$

Where m and g are defined as before, $\Delta t$ is the time interval between measurements for the convenient case of uniform time intervals (in seconds), i is a non-negative integer, $F_c[i]$ is the cutting force (in Newtons) at an elapsed test time of i*Δt, x[i] is the position of sample holder 24 and sample 28 measured at the same elapsed time (in meters), x[i+1] is the position of the same at the next time increment (in meters), and x[i−1] is the position of the same at the previous time increment (in meters). A plot of $F_c[i]$ versus time or some measure of the dispersion of the cutting force values (e.g. standard deviation, minimum, maximum, range) provides an indication of the local inhomogeneity in cut resistance of the sample. The temporal position data can also provide verification that the frictional forces in the guide apparatus are negligible via a comparison of the actual measured acceleration through the free-falling section with the gravitational acceleration constant. This is useful as a test quality assurance measure. Furthermore, integration of $(F_c/L)dx$ over the cutting distance provides the energy dissipated by the sample (or work performed by the knife) per unit length of sample in the direction of sample holder 24 movement. Subtracting this work from the total energy per unit length E/L calculated previously reveals the energy dissipated by the sample in the other two orthogonal directions which may provide additional useful information about the sample.

If desired, the configuration of the device described above may be modified in any suitable way. For example, the sample holder 24 may traverse a path that is not substantially vertical and/or linear. In addition, the sample holder 24 and the sample 28 may be stationary and the blade holder 22 and the blade 26 may be movable or the components may all be movable to obtain the desired relative movement of the sample 28 and the blade 26. Still further, the device may not depend upon gravity to impart kinetic energy so as to obtain the desired relative movement; instead, the kinetic energy may be supplied by one or a combination of two or more external influences or forces, such as a gravitational field, a magnetic field, an electrical or electromagnetic field, a pneumatic element, a mechanical element or apparatus, (such as one or more spring(s) acting on one or more component(s)), etc . . . .

Referring next to FIGS. 2–6, the sample holder 24 is mounted on a rail 40 and a rod 42 that guide the sample holder 24 along the path. The rail 40 and the rod 42 are secured to a support apparatus 43 including a support column 44 mounted on a support base 46 by angle members 48 and first and second support structures 50a, 50b extending between the support column 44 and the rail 40. Each support structure 50a, 50b includes a stand-off block 52a, 52b, respectively, secured to a rail block 54a, 54b, respectively, and the support column 44 by fasteners (not shown). The rail 40 is dumbbell-shaped in cross-section and is retained within elongate slots in the rail blocks 54a, 54b by bolts 56a, 56b disposed in bores 58a, 58b and extending though further bores (not shown) in a center or web portion 60 of the rail 40. The maximum thickness of the rail 40 is just slightly less than the width of the elongate slots in the rail blocks 54a, 54b so that the rail 40 is firmly and immovably retained therein.

Preferably, the rail 40 is a 36 inch Thomson Twin Rail System, model 2CA-08OKE L36, available from Applied Industrial Technologies of Saginaw, Mich.

A positioning station 70 is mounted on the support column 44 by a latch bracket 72 and fasteners 74 wherein the positioning station 70 includes a spring-loaded movable latch 76 (FIG. 5) actuable by a handle 78 to move into and out of interfering contact with a latch catch member 80 mounted to and carried by the sample holder 24. The position of the positioning station 70 may be adjusted by loosening the fasteners 74, thereby permitting the station 70 to be moved as a unit upwardly or downwardly on the support column 44. Once the station 70 is properly positioned, the fasteners 74 may be tightened to secure the station 70 in place.

The sample holder 24 includes a sample plate 90 secured to a bearing block 92 by fasteners. The bearing block 92 includes an elongate slot 94 extending therethrough wherein the rail 40 is snugly yet slidably received in the slot 94. Preferably, the rail 40 and the slot 94 are sized and shaped relative to one another and the materials and interfacing surfaces are designed so that that bearings and/or lubricating agents are not required to permit free relative movement of the bearing block 92 and the rail 40. Alternatively, bearings and/or lubricating agents may be used, if desired, provided that such elements do not adversely affect the operation of the device.

The latch catch member 80 is secured to a bracket 96, and the latter is secured to the bearing block 92 by fasteners (not shown). The bracket 96 may mount optional structure as noted on greater detail hereinafter. The bracket 96 includes a recess 98 through which the rod 42 extends, thereby permitting free motion of the bearing block 92 relative to the rail 40 without interference of the bracket 96 with the rod 42.

The sample plate 90 includes upper and lower mounting assemblies 100, 102 that mount a sample to the sample plate 90. The upper mounting assembly 100 includes a clamping plate 104 mounted to an upper surface 106 of the sample plate 90 by thumb screws 108. The lower mounting assembly 102 includes first and second side brackets 110, 112 mounted to the plate 90 by fasteners. Each of the side brackets 110, 112 further includes an inclined elongate slot 114, 116, respectively (FIG. 4A shows the side bracket 12 and associated apparatus in detail). A cylindrical locking bar 118 includes end portions 120a, 120b disposed in the inclined slots 114, 116. First and second springs 122, 124 are disposed in the inclined slots 114, 116, respectively, and bear against the end portions 120a, 120b to cause the locking bar 118 to be biased against ends 126, 128 of the slots 114, 116. When the locking bar 118 is in such position, a knurled center portion 130 of the locking bar 118 is in resilient contact with a rear surface 132 of the sample plate 90.

Figure 2:
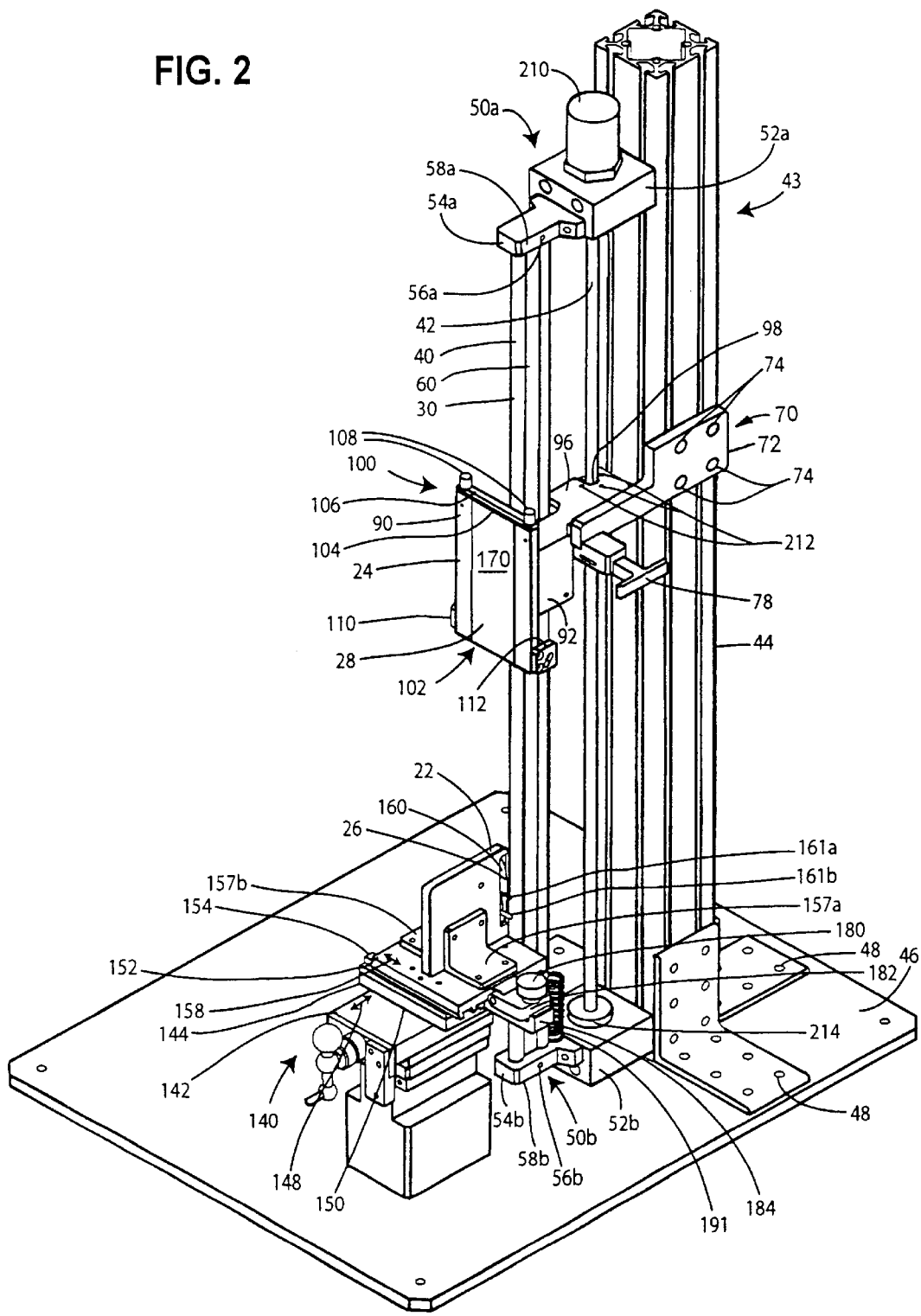
FIG. 2 is an isometric front view of a device in accordance with the block diagram of FIG. 1 with a sample holder shown in a latched, upper position.
Figure 3:
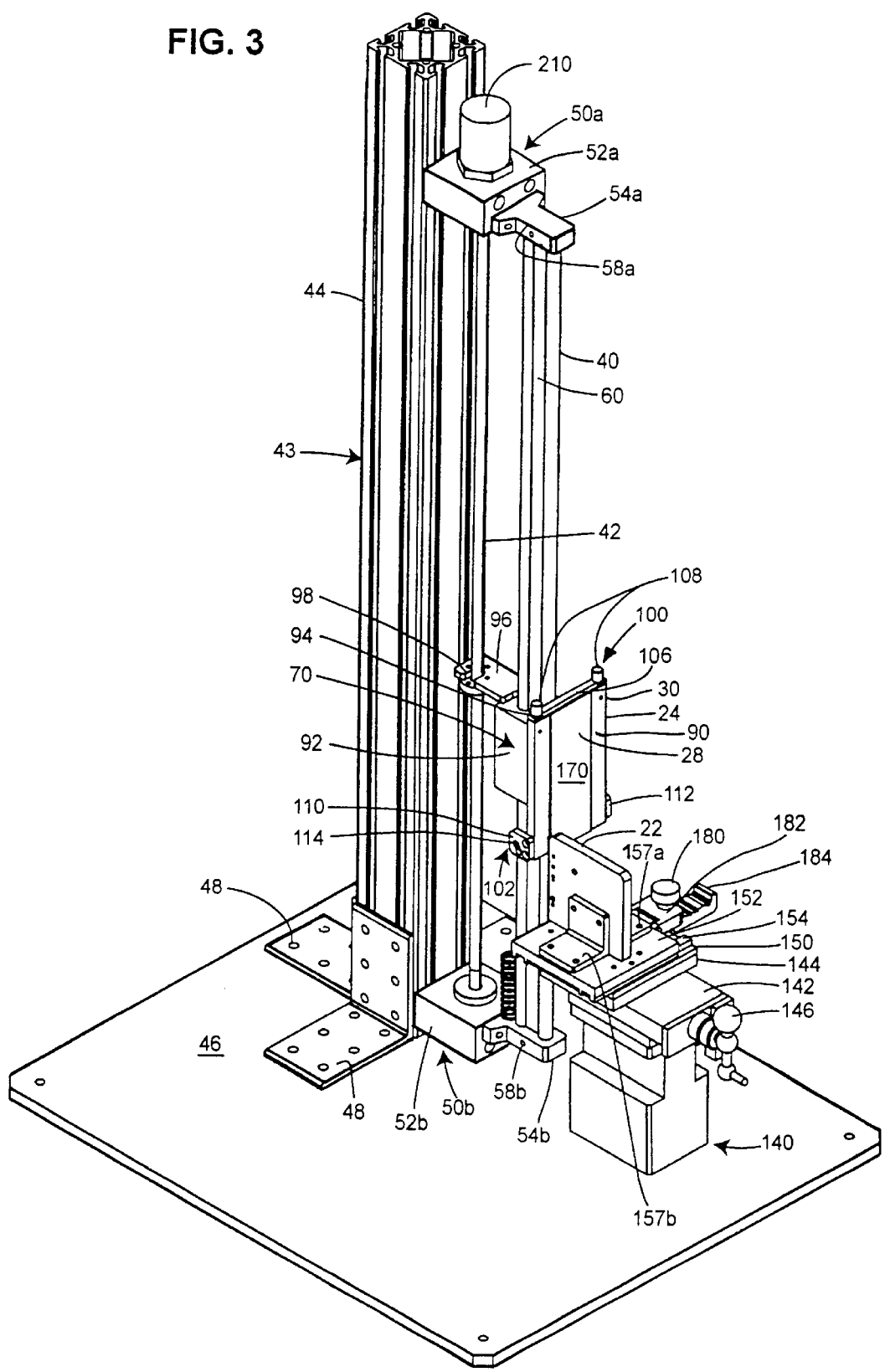
FIG. 3 is an isometric rear view of a device in accordance with the block diagram of FIG. 1 with the sample holder shown in an unlatched position.

Preferably, although not necessarily, the blade holder 22 is mounted on a movable and adjustable support apparatus 140. The support apparatus 140 includes a first support table 142 mounted on the support base 46 and a second support table 144 mounted on the first support table. The first support table 142 includes a rotary adjustment knob 146 that may be turned by an operator to permit movement of the blade 26 along a first direction indicated by arrows 148 (FIG. 2). The second support table 144 includes a base table portion 150 mounted on the first support table 142 and an upper table portion 152 mounted by linear slides 154, 156 to the base table portion 150. The blade holder 22 is mounted by brackets 157a, 157b and fasteners to the upper table portion 152. The linear slides 154, 156 include bearings (not shown) that permit movement of the upper table portion 152, and thus the blade 26, relative to the base table portion 150 along a second direction indicated by arrows 158 (FIG. 2). Preferably, the second direction is transverse to, and, more preferably, perpendicular to, the first direction. A spring (not shown) is connected between the upper table portion 152 and the base table portion 150 in a space therebetween to bias the upper table portion 152 toward an aligned position (seen in FIG. 2) relative to the base table portion 150.

Preferably the base table portion 150 is adjusted prior to use of the device to properly space the edge of the blade 26 from the sample holder 24. The base table portion is available from Milwaukee Slide and Spindle of Milwaukee, Wis., under part number R346L and the upper table portion 152 is available from McMaster Carr Supply Company of Aurora, Ohio under part number 60935K18.

INDUSTRIAL APPLICABILITY

Figure 6:
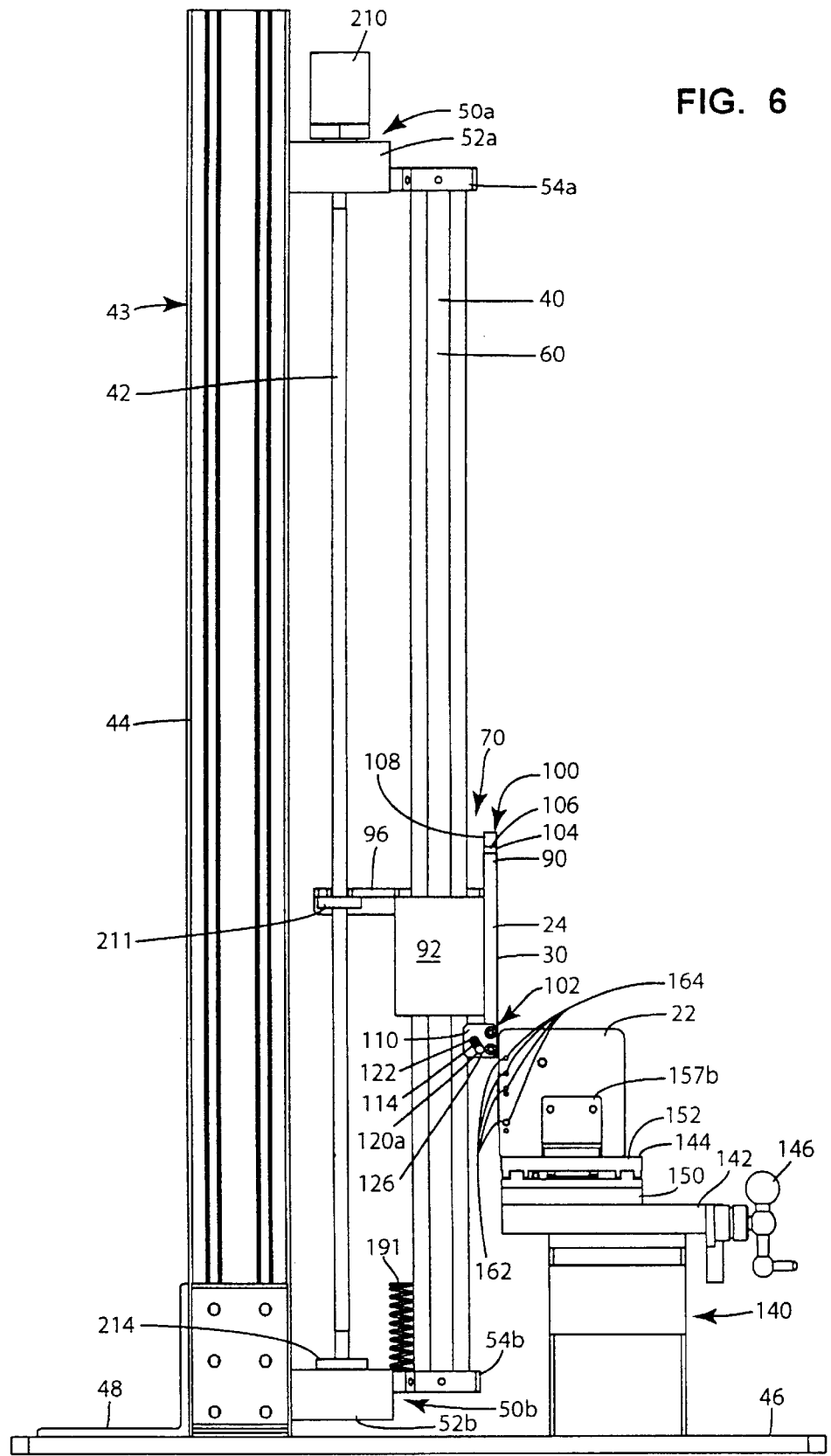
FIG. 6 is a rear elevational view of the device of FIG. 3.

The device of the present invention is prepared for use by moving the sample holder to the latched position as seen in FIG. 2. The operator pulls the handle 78 to retract the latch 76 and the operator raises the sample holder 24 to a position such that the latch catch member 80 is spaced above the latch 76. The handle 78 is then released to extend the latch 76 and the sample holder 24 is lowered until the latch catch member 80 rests on the latch 76. The operator then mounts the blade 26 in a blade recess 160 (FIG. 2) formed in the blade holder 22. Preferably, as seen in FIG. 6, a series of magnets 162 are disposed in recesses 164 in the blade holder 22 and firmly hold the blade 26 in position. Spaced dowel pins 161a, 161b (FIG. 2) are mounted in the blade holder 22 and extend into the blade recess 160 and further extend through a center aperture or slot 26a (FIG. 4) of the blade 26. The dowel pins 161a, 161b accurately position the blade 26. The blade may comprise a blade sold by Personna, Poultry Blades Code #88-0337. The blade holder can be modified to accept any type of cutting blade that has a curved or sloped lead in edge portion that permits the sample to be guided under the blade. Also, the blade should be fabricated with sufficient tolerances from blade to blade so that the test set-up does not need adjustment after each blade change.

Figure 7:
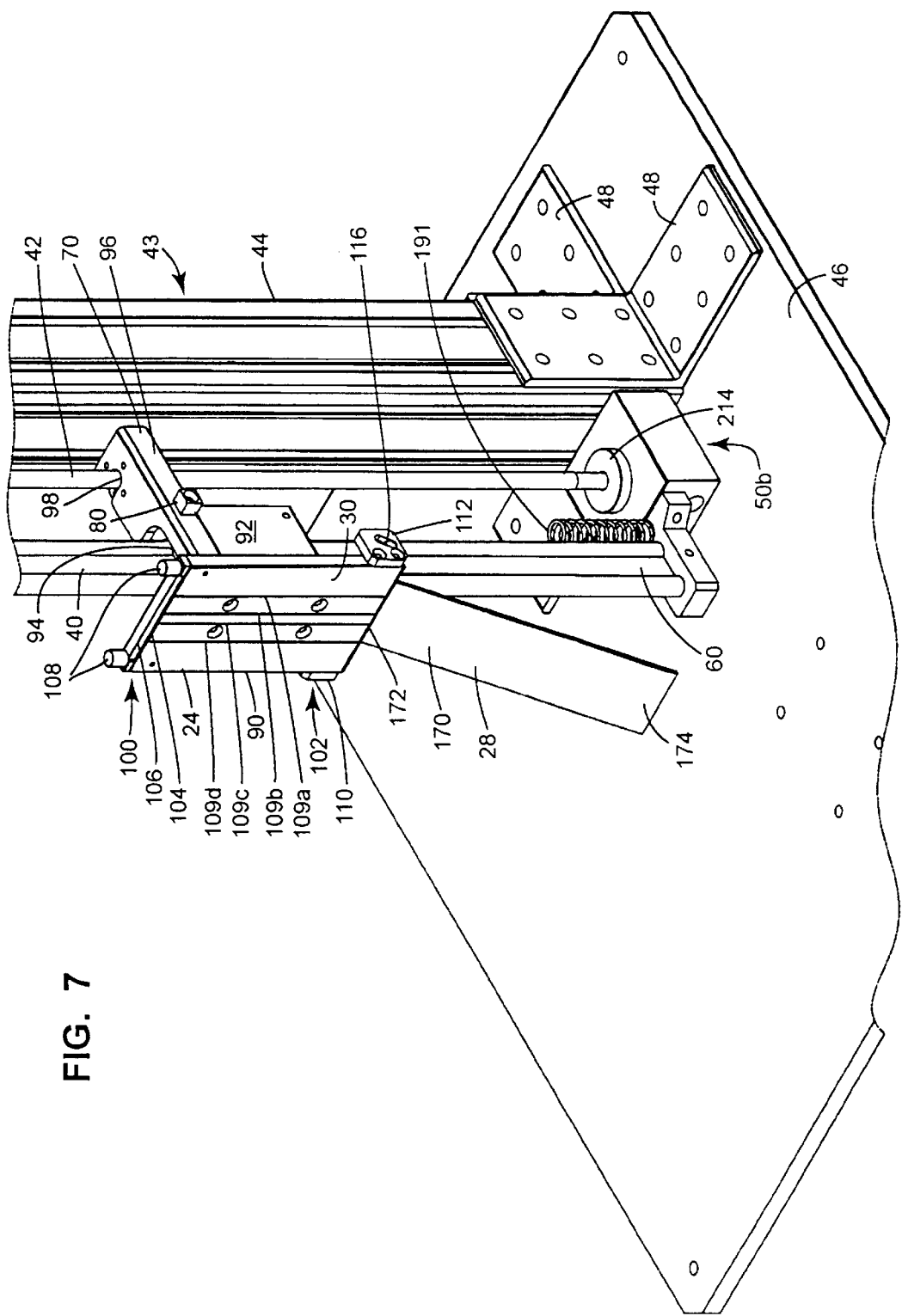
FIGS. 7–9 are enlarged, fragmentary, isometric views of the sample holder of FIG. 2 illustrating the process of mounting a sample thereon.
Figure 8:
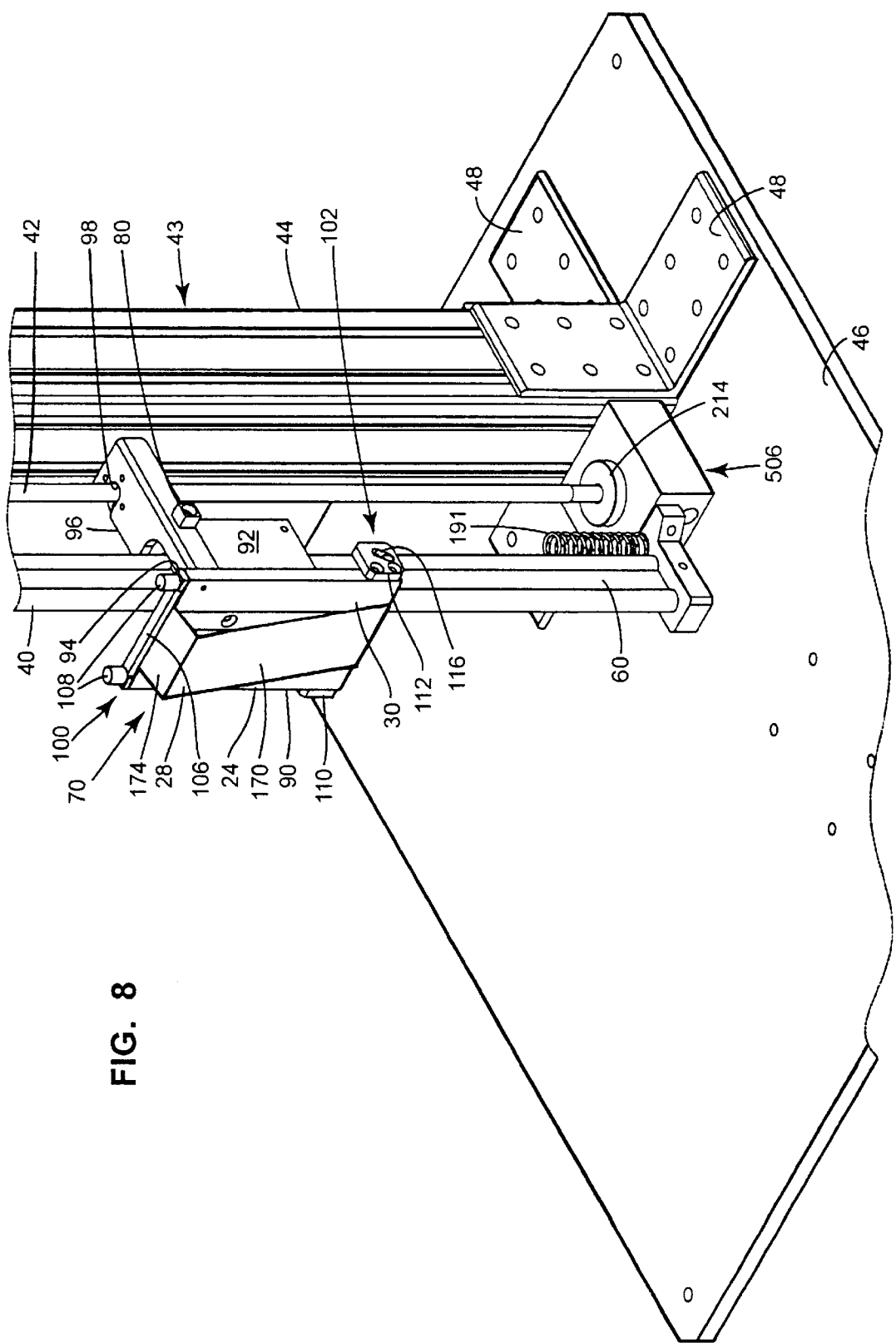
Figure 9:
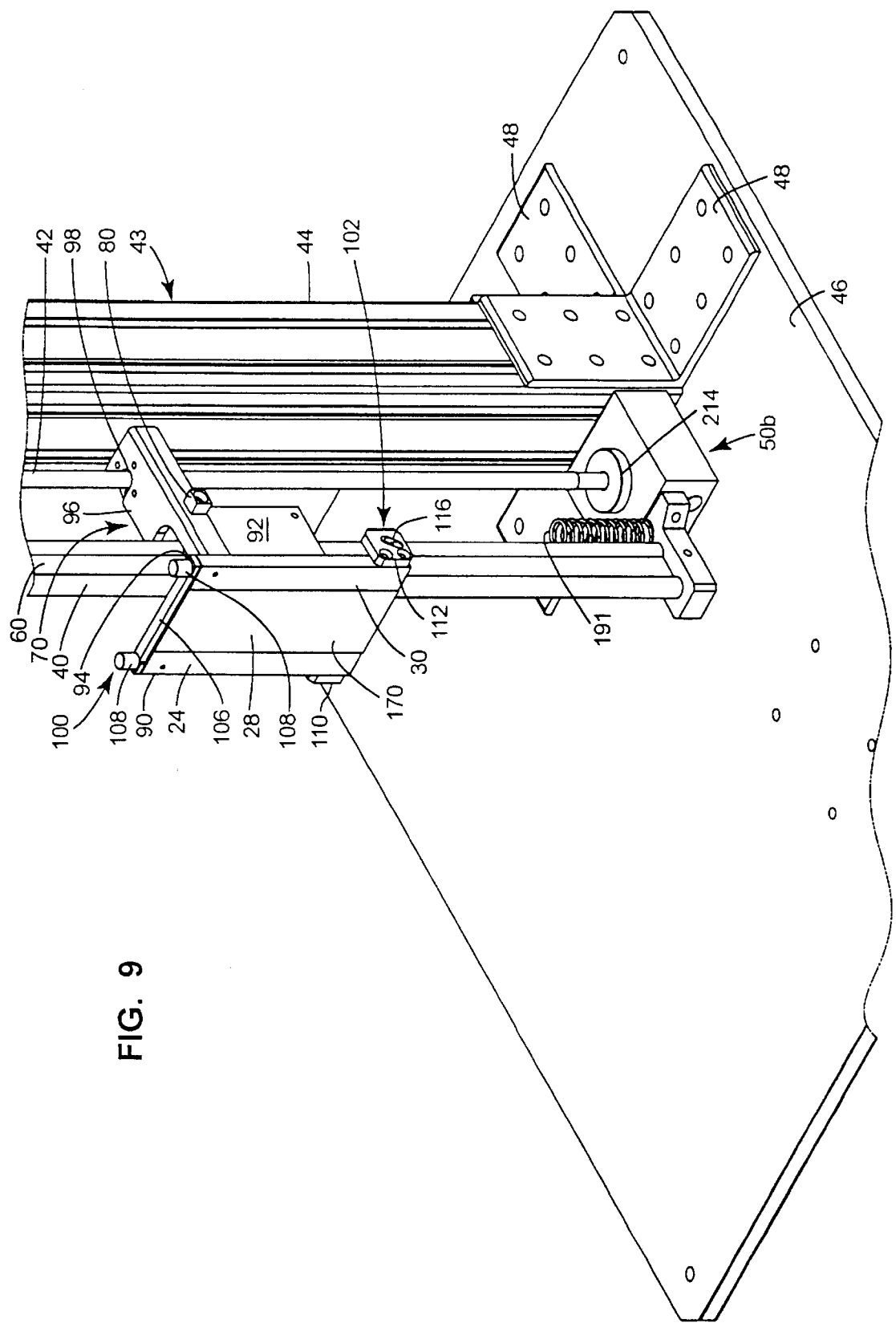

Once the blade 26 is mounted, (or before the blade is mounted, if desired) the device is further prepared for testing by mounting a sample 170 of a material on the sample holder 24 in accordance with the steps shown in FIGS. 7–9. Specifically, the cylindrical locking bar 118 is displaced by the operator such that the knurled center portion 130 is spaced from the rear surface 132 of the sample plate 90. The operator then inserts one end 172 of the sample 170 into the space between the center portion 130 and the rear surface 132 and releases the locking bar 118, whereupon the end 172 of the sample 170 is captured by the knurled center portion 130 against the rear surface 132. The sample 170 is then positioned as shown in FIG. 7. Thereafter, the operator may insert an opposite end 174 of the sample 170 into a space between the clamping plate 14 and the upper surface 106 of the sample plate 90 (FIG. 8), pull the sample tight over the side surface 30 and tighten the thumb screws 108 to fix the sample 170 in position (FIG. 9).

Figure 12:
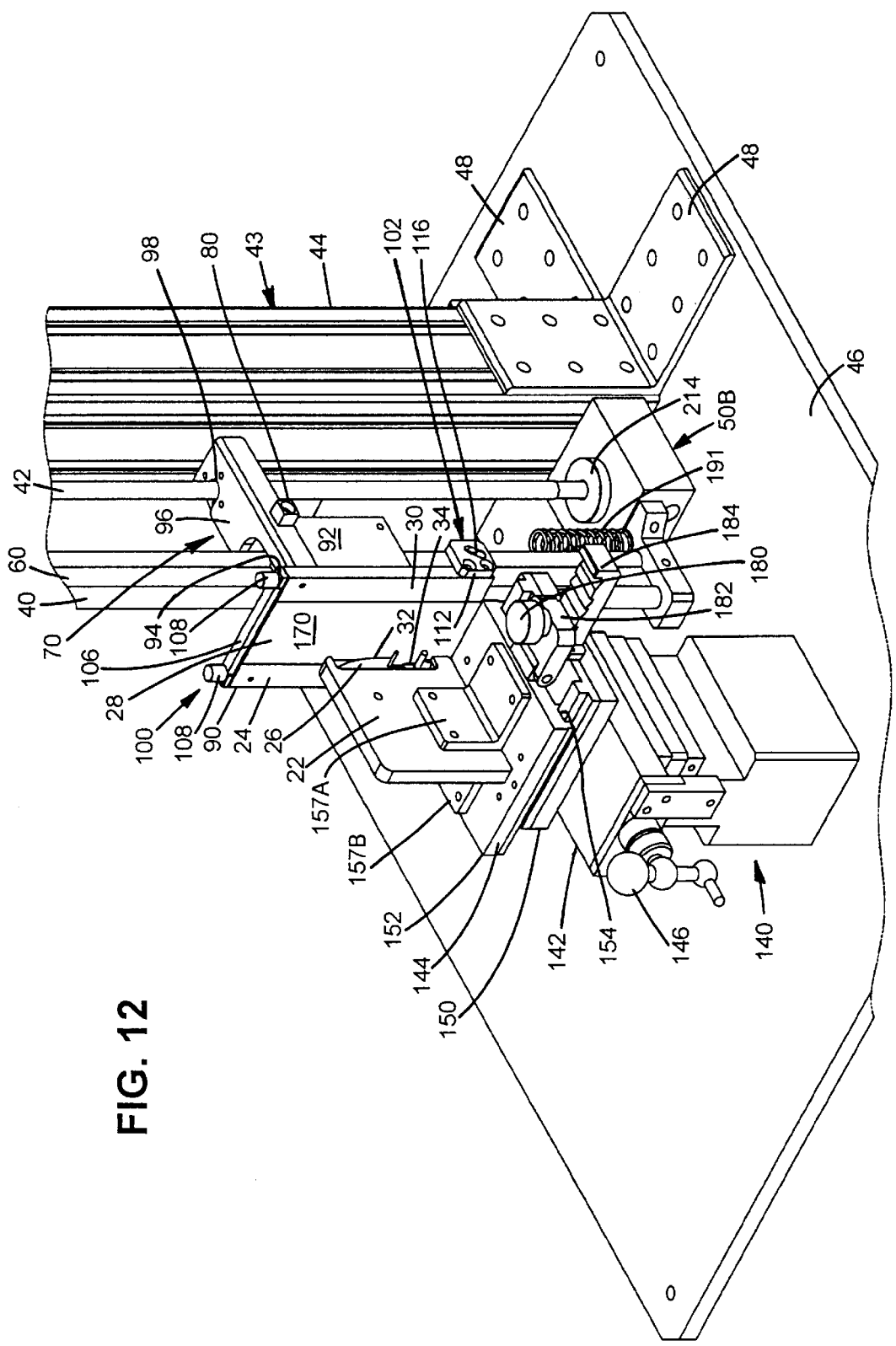

Testing is initiated in the case of a new and previously unused blade 26 by positioning the upper table portion 152 at the aligned position seen in FIG. 2 relative to the base table portion 150. This positioning is accomplished by pulling a knob 180 secured to a pawl member 182 upwardly, thereby spacing the pawl member 182 from a toothed rack member 184 and permitting relative movement of the upper table portion 152 and the base table portion along the second direction. The pawl member 182 and the toothed rack member 184 are positionable in one of four stable latched positions, thereby resulting in positioning of the blade 26 via the upper table portion 152 in one of four paths relative to the sample 170. Once the upper table portion 152 is properly positioned, the knob 180 is released, thereby causing the pawl member 182 to move into locking engagement with the toothed rack member 184. This, in turn, locks the upper table portion 152 in the aligned position, thereby causing the blade to be locked in a first one of the four paths. The operator then pulls the handle 78 outwardly to move the latch 76 out of interfering relationship with the latch catch member 80. The sample holder 24 immediately moves under the influence of gravity downwardly until the sample 170 contacts the blade 26. Movement continues until the kinetic energy of the sample holder 24 is exhausted, as noted above, and as shown in FIG. 12. As seen in FIG. 7, four parallel longitudinal grooves 190a–190d are formed in the side surface 30 and coincide with the four paths of the blade 26 relative to the sample holder 24 when the upper table portion 152 is disposed in the four latched positions. Preferably, the depths of the grooves are substantially equal and sufficient to permit the blade 26 to cut the sample 170 without contacting the sample holder 24.

As noted above, the height of the positioning station 70 is adjusted so that the kinetic energy of the sample holder 24 is used up while the blade 26 is in contact with the sample and while the blade 26 is positioned in one of the grooves 190. This insures that accurate readings are obtained. A spring 191 is provided that prevents direct contact of the sample holder 24 with the support member 50 in the event that the sample holder 24 is released from a height that would result in continued motion of the sample holder 24 even after cutting of the full length of the sample 170.

Figure 10:
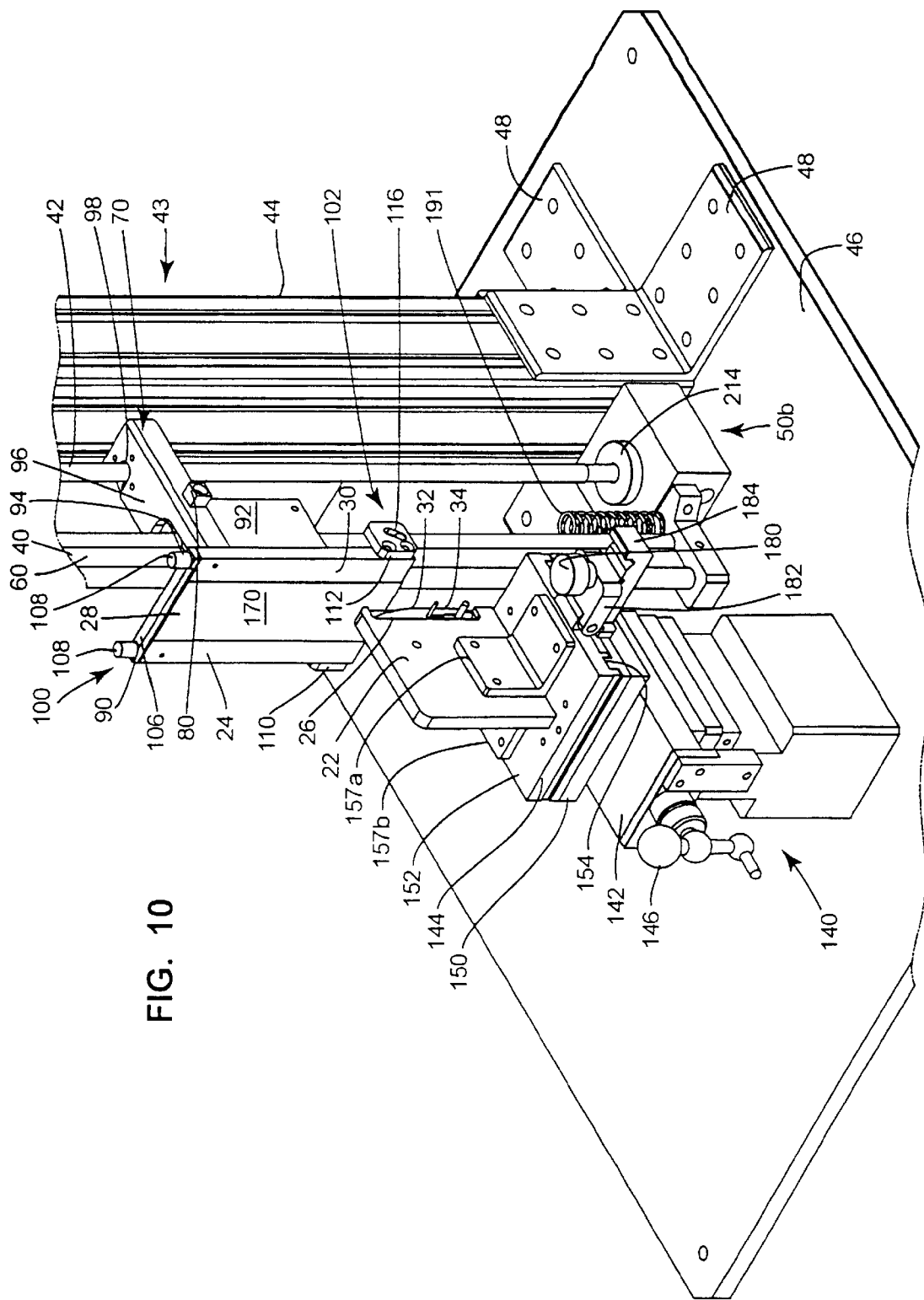
Figure 11:
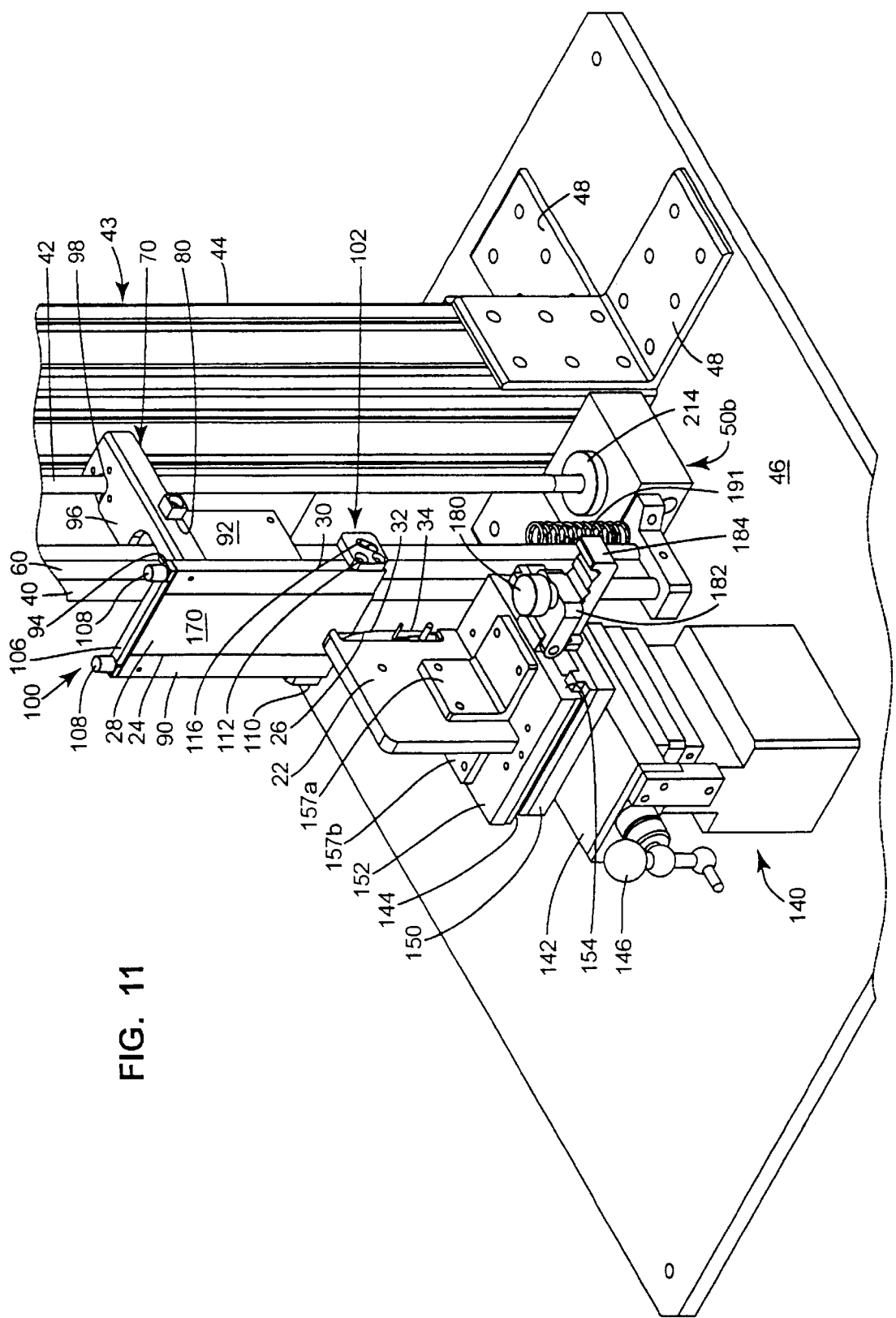

The first cut or slice operation described above is undertaken to remove any burrs that may be on the edge of the blade 26. Thereafter, three successive further cut or slice operations are effected with the blade sequentially disposed in the remaining three paths and with the slice operations otherwise being conducted in identical fashion to the procedure described above and with the positioning station 70 located at the same height as in the first slice or cut operation. Specifically, during a second cut or slice operation, the pawl member 182 and the toothed rack member 184 are positioned in a second one of the four stable latched positions as seen in FIG. 10, thereby resulting in positioning of the blade 26 via the upper table portion 152 in a second of the four paths relative to the sample 170. The cut or slice operation is then undertaken as noted above. Thereafter, the pawl member 182 and the toothed rack member 184 are positioned in a third of the four stable latched positions (FIG. 11), thereby resulting in positioning of the blade 26 in a third of the four paths relative to the sample 170 and the slice or cut operation is repeated. Lastly, the pawl member 182 and the toothed rack member 184 are positioned in a fourth of the four latched positions (shown in FIG. 12), thereby causing positioning of the blade 26 in the fourth path relative to the sample 170. The slice or cut operation is then repeated again.

Figure 4:
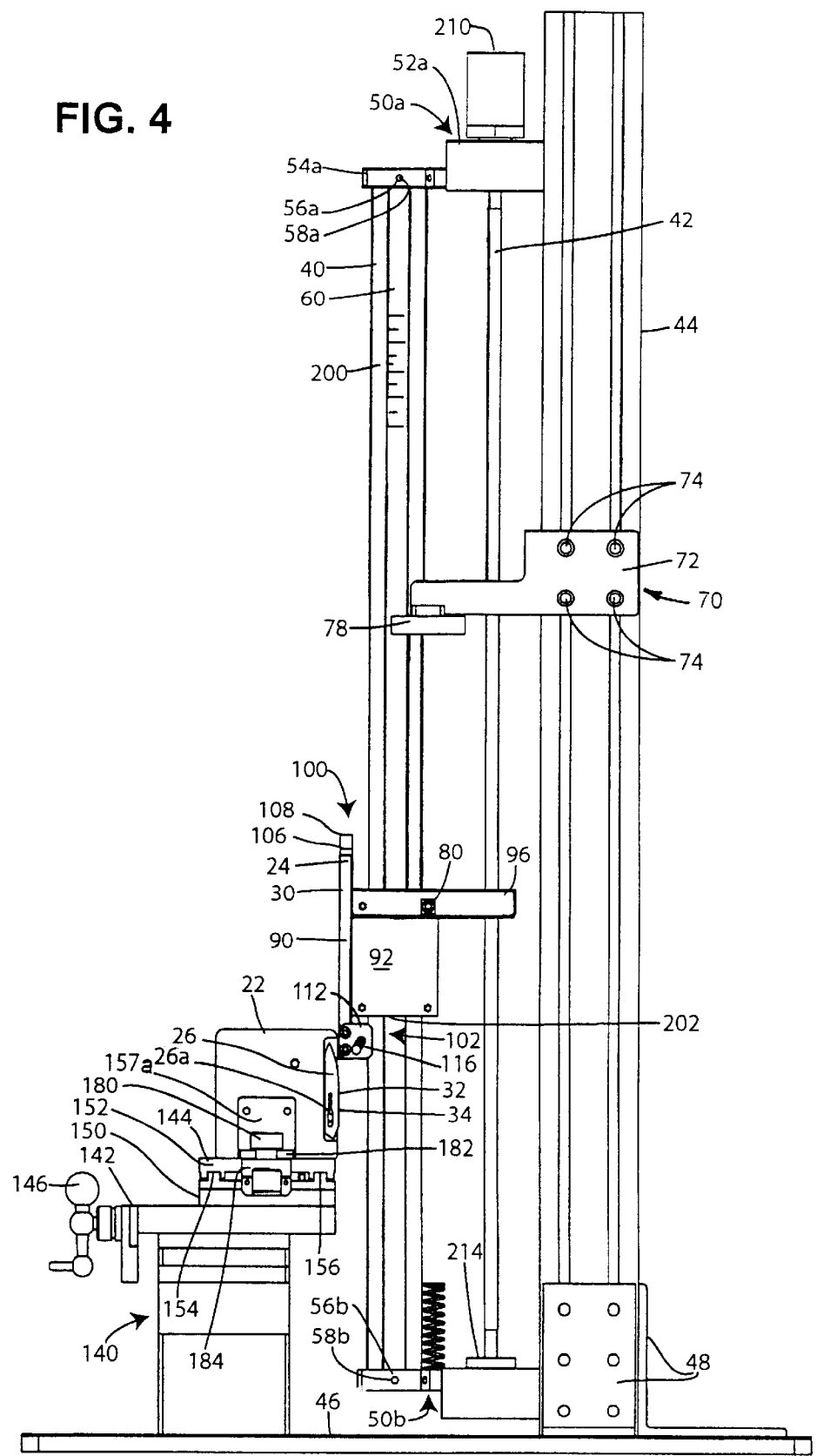
FIG. 4 is a front elevational view of the device of FIG. 3.

Following each slice or cut operation, the length of travel H of the sample holder 24 and the length L of the slice or cut are measured. L is measured directly in any desired manner. Measurement of the length H may be facilitated by a ruler 200 (a portion of which is shown in FIG. 4), which is mounted on the web portion 60 of the rail as seen in FIG. 4. Each value of H is obtained by noting on the ruler 200 the position D1 of a particular point of the sample holder 24, such as a lower edge 202 thereof (FIG. 4), before the slice or cut operation, and further noting the position D2 of the same point 202 of the sample holder on the ruler 200 at the end of the slice or cut operation. Each value H is then obtained as the difference D2−D1. The resulting values for H and L are used to calculate slice resistance values as noted above. The slice resistance values are averaged to obtain a single value for the sample representing the slice resistance thereof.

If desired, the values of H can be automatically obtained by providing an optional distance sensor 210 (FIGS. 2–6) that senses H by detecting the starting and ending positions of the moving element. One suitable sensor, employing the principle of magnetostriction, has a disk-shaped toroidal magnet 211 (FIG. 6) surrounding the rod 42 and secured by fasteners 212 (FIG. 2) to an underside of the bracket 96. It should be noted that, if this type of distance sensor 210 is used, an electrically insulative insert 214 must be provided to mount the rod 42 to the support base 46. The distance sensor 210 and the rod 42 may comprise a Temposonics R-series sensor sold by MTS Systems Corporation of Cary, N.C. under part number RHT0330URG01V011000 and the magnet is sold by the same company under part number 201542.

The present invention, as described above, is effective to develop a measure of cut or slice resistance for samples of substantially equal thicknesses. If it is desired to develop indications of slice or cut resistance of samples of different thicknesses, one could do so using the apparatus of the present invention in accordance with the equation:

$$E/(LT) = mgH/(LT)$$

where T is the thickness of the particular sample and the remaining values are as described above.

The present invention obtains cut resistance values by cutting into a sample in a first direction as a result of relative movement of a blade and a sample resulting from application of force in a second, different direction. The present invention can measure any suitable parameter of the relative movement to obtain the cut resistance values. In addition, the present invention can be used to determine slice or cut resistance of non-homogeneous materials in a simple and effective manner.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A device for determining a cut resistance of a sample, comprising:
    a blade wherein the blade and the sample are relatively movable along a linear path;
    a first apparatus that transfers energy to at least one of the sample and the blade to cause relative movement thereof in a direction parallel to a surface of the sample such that the blade contacts and cuts the sample until the imparted energy is expended and relative movement is terminated; and
    a second apparatus that measures a parameter of the relative movement to obtain an indication of the cut resistance of the sample.

2. The device of claim 1, further including a sample holder wherein the sample is attached to the sample holder.

3. A device for determining a cut resistance of a sample, comprising:
    a blade wherein the blade and the sample are relatively movable;
    a first apparatus that transfers energy to at least one of the sample and the blade to cause relative movement thereof in a direction parallel to a surface of the sample, wherein the relative movement occurs along a substantially vertical path such that the blade contacts and cuts the sample until the imparted energy is expended and relative movement is terminated;
    a second apparatus that measures a parameter of the relative movement to obtain an indication of the cut resistance of the sample; and
    a sample holder wherein the sample is attached to the sample holder.

4. The device of claim 3, wherein the first apparatus releases the sample holder at a predetermined height above the blade whereby gravity imparts energy to the sample.

5. The device of claim 4, wherein the sample has a particular thickness and the sample holder is spaced from an edge of the blade by a distance less than the particular thickness.

6. The device of claim 3, wherein the second apparatus determines a length of the path.

7. A device for determining a cut resistance of a sample, comprising:
    a blade wherein the blade and the sample are relatively movable;
    a first apparatus that transfers energy to at least one of the sample and the blade to cause relative movement thereof in a direction parallel to a surface of the sample, said first apparatus guiding the sample along a substantially vertical path such that the blade contacts and cuts the sample until the imparted energy is expended and relative movement is terminated; and
    a second apparatus that measures a parameter of the relative movement to obtain an indication of the cut resistance of the sample.

8. A device for determining a cut resistance of a sample, comprising:
    a blade wherein the blade and the sample are relatively movable;
    a first apparatus that transfers energy to at least one of the sample and the blade to cause relative movement thereof in a direction parallel to a surface of the sample, said first apparatus guiding the sample along a substantially vertical linear path such that the blade contacts and cuts the sample until the imparted energy is expended and relative movement is terminated; and
    a second apparatus that measures a parameter of the relative movement to obtain an indication of the cut resistance of the sample.

9. A device for determining cut resistance of a material, comprising
    a sample holder having a known mass wherein the sample holder is adapted to receive a sample of the material;
    a blade;
    guide apparatus for effecting relative movement of the sample holder and the blade holder under the influence of gravity along a path from a particular initial position wherein the material sample is out of contact with the blade and a final position wherein the material sample is in stationary contact with the blade thereby forming a cut having a cut length in the sample; and
    measurement apparatus for indicating a length of the path, the path length and the cut length being used to obtain an indication of cut resistance.

10. The device of claim 9, wherein the path is substantially vertical.

11. The device of claim 9, wherein the guide apparatus comprises a track.

12. The device of claim 9, wherein the material sample has a particular thickness and the sample holder is spaced from an edge of the blade by a distance less than the particular thickness.

13. The device of claim 9, further including a blade holder wherein the blade is mounted to the blade holder.

14. A method of determining a cut resistance of a material, the method comprising the steps of:

providing a sample of the material and a blade wherein the sample and the blade are relatively movable along a linear path;

imparting energy to at least one of the sample and the blade to cause relative movement thereof in a direction parallel to a surface of the sample such that the blade contacts and cuts the sample until the imparted energy is expended and relative movement is terminated; and measuring a parameter of the relative movement to obtain an indication of the cut resistance of the sample.

15. The method of claim 14, further including the step of providing a sample holder wherein the sample is attached to the sample holder.

16. A method of determining a cut resistance of a material, the method comprising the steps of:

providing a sample of the material and a blade wherein the sample and the blade are relatively movable;

providing a sample holder wherein the sample is attached to the sample holder;

imparting energy to at least one of the sample and the blade to cause relative movement thereof in a direction parallel to a surface of the sample, wherein the relative movement occurs along a substantially vertical path, such that the blade contacts and cuts the sample until the imparted energy is expended and relative movement is terminated; and measuring a parameter of the relative movement to obtain an indication of the cut resistance of the sample.

17. The method of claim 16, wherein the step of imparting includes the step of releasing the sample holder at a predetermined height above the blade.

18. The method of claim 17, wherein the relative movement occurs along a path having a path length and wherein the step of measuring includes the step of determining the path length.

19. The method of claim 17, wherein the relative movement occurs along a path and the step of measuring includes the step of measuring the position of the moving element(s) at multiple times throughout the test.

20. The method of claim 17, including the further step of guiding the sample along a substantially vertical path.

21. The method of claim 17, including the further step of guiding the sample along a substantially vertical linear path.

22. The method of claim 17, including the further step of providing a guide apparatus that guides the sample during movement thereof.

23. The method of claim 22, wherein the guide apparatus comprises a track.

24. The method of claim 17, wherein the sample is mounted on a mounting surface of a movable sample holder and wherein the sample has a particular thickness and the mounting surface is spaced from an edge of the blade by a distance less than the particular thickness.

25. A method of determining a cut resistance of a material, the method comprising the steps of:

providing a movable sample holder having a known mass wherein the sample holder is adapted to receive a sample of the material;

providing a stationary blade holder and a blade mounted to the blade holder;

positioning the movable sample holder at a predetermined height above the blade;

releasing the movable sample holder to cause the sample holder to move under the influence of gravity until the sample contacts the blade and is cut thereby for a cut distance until movement of the sample holder is terminated; and using the cut distance and the predetermined height to obtain an indication of the cut resistance of the sample.

26. The method of claim 25, including the further step of guiding the movable sample holder during movement thereof.

27. The method of claim 26, wherein the movable sample holder traverses a substantially vertical path during movement thereof.

28. The method of claim 26, wherein the movable sample holder traverses a substantially vertical linear path during movement thereof.

29. The method of claim 25, including the further step of providing a guide apparatus that guides the sample during movement thereof.

30. The method of claim 29, wherein the guide apparatus comprises a track.

31. The method of claim 25, wherein the sample is mounted on a mounting surface of a movable sample holder and wherein the sample has a particular thickness and the mounting surface is spaced from an edge of the blade by a distance less than the particular thickness.

32. A method of determining cut resistance inhomogeneity of a material, the method including the steps of:

providing a sample of the material and a blade wherein the sample and the blade are relatively movable;

imparting energy to at least one of the sample and the blade to cause relative movement thereof in a direction parallel to a surface of the sample such that the blade contacts and cuts the sample until the imparted energy is expended and relative movement is terminated; and measuring the position of the at least one of the sample and the blade to obtain an indication of the local inhomogeneity of cut resistance of the sample.

33. The method of claim 32, wherein the step of measuring comprises the step of detecting the movement of the at least one of the sample and blade over time.

* * * * *